(12) United States Patent
Sugaya et al.

(10) Patent No.: US 9,243,226 B2
(45) Date of Patent: Jan. 26, 2016

(54) BIASING OF CELLS TOWARD RETINAL, CORNEAL OR LENS DEVELOPMENT

(75) Inventors: Kiminobu Sugaya, Winter Park, FL (US); Angel Alvarez, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 306 days.

(21) Appl. No.: 12/036,722

(22) Filed: Feb. 25, 2008

(65) Prior Publication Data

US 2008/0233648 A1   Sep. 25, 2008

Related U.S. Application Data

(60) Provisional application No. 60/891,354, filed on Feb. 23, 2007.

(51) Int. Cl.
| | |
|---|---|
| *C12N 15/85* | (2006.01) |
| *C12N 5/079* | (2010.01) |
| *A61K 48/00* | (2006.01) |

(52) U.S. Cl.
CPC ............ *C12N 5/0621* (2013.01); *A61K 48/005* (2013.01); *C12N 2510/00* (2013.01)

(58) Field of Classification Search
None
See application file for complete search history.

(56) References Cited

PUBLICATIONS

Kondoh (Develop. Growth Differ. 2008, vol. 50, pp. S57-S69).*
Ogino and Yasuda (Develop. Growth Differ. 2000. vol. 42, pp. 437-448).*
Akimoto M., "Transcriptional Factors Involved in Photoreceptor Differentiation", Semin Ophthalmol, Jan.-Mar. 2005, vol. 20, pp. 25-30.
Akagi T, et al., "Otx2 homeobox gene induces photoreceptor-specific phenotypes in cells derived from adult iris and ciliary tissue", Invest Ophthalmol Vis Sci, Dec. 2004, vol. 45(12), pp. 4570-4575.
Chiambaretta F, et al., "Regulation of Corneal Keratin-12 Gene Expression by the Human Kruppel-like Transcription Factor 6", Invest Ophthalmol Vis Sci, Nov. 2002, vol. 43(11), pp. 3422-3429.
Chiambaretta F, et al., "Cell and tissue specific expression of human Kruppel-like transcription factors in human ocular surface", Mol Vis, Nov. 2004, vol. 10, pp. 901-909.
Collinson JM, et al., "The roles of Pax6 in the Cornea, Retina, and Olfactory Epithelium of the Developing Mouse Embryo", Dev Biol, Mar. 2003, vol. 255(2), pp. 303-312.
Dandona L, et al., "What is the global burden of visual impairment?" BMC Med, Mar. 16, 2006;4:6. Review.
Daniels JT, et al., "Corneal stem cells in review", Wound Repair Regen, Nov.-Dec. 2001, vol. 9(6), pp. 483-494.
Ikeda H, et al., "Generation of Rx+/Pax6+ neural retinal precursors from embryonic stem cells", Proc Natl Acad Sci U S A., Aug. 9, 2005, vol. 102(32), pp. 11331-11336.
Meyer JS, et al., "Stem cells for retinal degenerative disorders", Ann N Y Acad Sci., May 2005, vol. 1049, pp. 135-145.
Sivak JM, et al., "Transcription Factors Pax6 and AP-2alpha Interact to Coordinate Corneal Epithelial Repair by Controlling Expression of Matrix Metalloproteinase Gelatinase B", Mol Cell Biol, Jan. 2004, vol. 24(1), pp. 245-257.
Whitcher JP, et al., "Corneal blindness: a global perspective", Bull World Health Organ, 2001, vol. 79(3), pp. 214-221.

* cited by examiner

*Primary Examiner* — Celine Qian
(74) *Attorney, Agent, or Firm* — Timothy H. Van Dyke; Beusse, Wolter, Sanks & Maire, PLLC

(57) ABSTRACT

Methods are described that bias cells, such as potent and multipotent stem cells, by transfection with a nucleic acid sequence, to differentiate to a desired end-stage cell or a cell having characteristics of a desired end-stage cell. In particular embodiments, human neural stem cells or mesenchymal stem cells are transfected with vectors comprising genes in the homeobox family of transcription factor developmental control genes, and this results in a greater percentage of resultant transformed cells, or their progeny, differentiating into a desired end-stage cell or a cell having characteristics of a desired end-stage cell.

1 Claim, No Drawings

BIASING OF CELLS TOWARD RETINAL, CORNEAL OR LENS DEVELOPMENT

RELATED APPLICATIONS

This application claims priority to U.S. Ser. No. 60/891,354 filed Feb. 23, 2007, which is incorporated herein by reference.

FIELD OF INVENTION

The present invention is directed to methods and systems directed to altering the differentiation of a cell, more particularly to biasing a multipotent stem cell by transfecting the cell with a nucleic acid sequence comprising a desired gene, the gene being expressed so that the cell, or its progeny, differentiate to a desired end-stage cell.

BACKGROUND

Proper cellular function and differentiation depends on intrinsic signals and extracellular environmental cues. These signals and cues vary over time and location in a developing organism (i.e., during embryogenesis), and remain important in developing and differentiating cells during post-natal growth and in a mature adult organism. Thus, in a general sense, the interplay of the dynamically changing set of intracellular dynamics (such as manifested by intrinsic chemical signaling and control of gene expression) and environmental influences (such as signals from adjacent cells) determine cellular activity. The cellular activity so determined is known to include cell migration, cell differentiation, and the manner a cell interacts with surrounding cells.

The use of stem cells and stem-cell-like cells of various types for cell replacement therapies, and for other cell-introduction-based therapies, is being actively pursued by a number of researchers. Embryonic stems cells from a blastocyst stage are frequently touted for their pluripotency—that is, their ability to differentiate into all cell types of the developing organism. Later-stage embryonic stem cells, and certain cells from generative areas of an adult organism, are identified as more specialized, multipotent stem cells. These cells include cells that are able to give rise to a succession of a more limited subset of mature end-stage differentiated cells of particular types or categories, such as hematopoietic, mesenchymal, or neuroectodermal end-stage differentiated cells. For example, a multipotent neural stem cell may give rise to one or more neuron cell types (i.e., cholinergic neuron, dopaminergic neuron, GABAergic neurons), which includes their specific cell classes (i.e., a basket cell or a chandelier cell for GABAergic neurons), and to non-neuron glial cells, such as astrocytes and dendrocytes.

Further along the path of differentiation are cells derived from multipotent stem cells. For example, derivatives of a localized, non-migrating neuroectodermal type stem cell may migrate but, compared to their multipotent parent, have more limited abilities to self-renew and to differentiate (See Stem Cell Biology, Marshak, Gardner & Gottlieb, Cold Spring Harbor Laboratory Press, 2001, particularly Chapter 18, p. 407). Some of these cells are referred to a neuron-restricted precursors ("NRPs"), based on their ability, under appropriate conditions, to differentiate into neurons. There is evidence that these NRPs have different subclasses, although this may reflect different characteristics of localized multipotent stem cells (Stem Cell Biology, Marshak et al., pp 418-419).

One advantage of use of mulitpotent and more committed cells further along in differentiation, compared to pluripotent embryonic stem cells, is the reduced possibility that some cells introduced into an organism from such source will form a tumor (Stem Cell Biology, Marshak et al., p. 407). However, a disadvantage of cells such as cell types developed from multipotent stem cells, for instance, embryonic progenitor cells, is that they are not amenable to ongoing cell culture. For instance, embryonic neural progenitor cells, which are able to differentiate into neurons and astrocytes, are reported to survive only one to two months in a cell culture.

There is a need in the art to improve the compositions, methods and systems that provide biased and/or differentiated cells from stem cells or stem-cell-like cells. More particularly, a need exists to obtain a higher percentage of desired cells from a pre-implantation cell culture, such as starting from multipotent stem cells and obtaining a higher percentage of cells committed to differentiate to a specified type of functional nerve cell, such as cholinergic neurons or inner ear hair cells. The present invention addresses these needs.

DETAILED DESCRIPTION

In reviewing the detailed disclosure which follows, and the specification more generally, it should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

DEFINITIONS

Stem cells are undifferentiated cells that exist in many tissues of embryos and adult organisms. In embryos, blastocyst stem cells are the source of cells that differentiate to form the specialized tissues and organs of the developing fetus. In adults, specialized stem cells in individual tissues are the source of new cells, replacing cells lost through cell death due to natural attrition, disease, or injury. Stem cells may be used as substrates for producing healthy tissue where a disease, disorder, or abnormal physical state has destroyed or damaged normal tissue.

Five defining characteristics of stem cells have been advanced (from Weiss et al., 1996). That is, stems cells generally are recognized as having the ability to:

1. Proliferate: Stem cells are capable of dividing to produce daughter cells.
2. Exhibit self-maintenance or renewal over the lifetime of the organism: Stem cells are capable of reproducing by dividing symmetrically or asymmetrically to produce new stem cells. Symmetric division occurs when one stem cell divides into two daughter stem cells. Asymmetric division occurs when one stem cell forms one new stem cell and one progenitor cell. Symmetric division is a source of renewal of stem cells. This permits stem cells to maintain a consistent level of stem cells in an embryo or adult mammal.

3. Generate large number of progeny: Stem cells may produce a large number of progeny through the transient amplification of a population of progenitor cells.

4. Retain their multilineage potential over time: The various lines of stem cells collectively are the ultimate source of differentiated tissue cells, so they retain their ability to produce multiple types of progenitor cells, which in turn develop into specialized tissue cells.

5. Generate new cells in response to injury or disease: This is essential in tissues which have a high turnover rate or which are more likely to be subject to injury or disease, such as the epithelium or blood cells.

Thus, key features of stem cells include their capability of self-renewal, and their capability to differentiate into a range of end-stage differentiated tissue cells.

By "neural stem cell" (NSC) is meant a cell that (i) has the potential of differentiating into at least two cell types selected from a neuron, an astrocyte, and an oligodendrocyte, and (ii) exhibits self-renewal, meaning that at a cell division, at least one of the two daughter cells will also be a stem cell. Generally, the non-stem cell progeny of a single NSC are capable of differentiating into neurons, astrocytes, Schwann cells, and oligodendrocytes. Hence, a stem cell such as a neural stem cell is considered "multipotent" because its progeny have multiple differentiative pathways. Under certain conditions an NSC also may have the potential to differentiate as another non-neuronal cell type (e.g., a skin cell, a hematopoietic cell, a smooth muscle cell, a cardiac muscle cell, a skeletal muscle cell, a bone cell, a cartilage cell, a pancreatic cell or an adipocyte).

By "Human Neural Stem Cell" ("HNSC") is meant a neural stem cell of human origin. A HNSC may be of fetal origin, or adult origin from a neural source, or may be derived from other cell sources, such as by de-differentiating a cell of mesenchymal origin. As to the latter, for example see U.S. application serial number 2003/0219898, which is incorporated by reference, inter alia, specifically for this teaching. HNSCs of the invention are distinguished from natural HNSCs by their adaptation for proliferation, migration and differentiation in mammalian host tissue when introduced thereto.

By a "population of cells" is meant a collection of at least ten cells. A population may consist of at least twenty cells, or of at least one hundred cells, or of at least one thousand or even one million cells. Because the NSCs of the present invention exhibit a capacity for self-renewal, they can be expanded in culture to produce a collection of large numbers of cells.

By "potent cell" is meant a stem cell that has the capability to differentiate into a number of different types of end-stage cell types, and to self-renew, and may include stem cells classified as pluripotent, multipotent, or cells more differentiated than multipotent (i.e., a dedicated progenitor) under different stem cell classification schemes.

By "a presumptive end-stage cell" is meant a cell that has acquired characteristics of a desired end-stage cell type, but which has not been conclusively identified as being the desired end-stage cell. A presumptive end-stage cell possesses at least two, and often more, morphological and/or molecular phenotypic properties of the desired end-stage cell.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Molecular Cloning A Laboratory Manual, $3^{rd}$ Ed., ed. by Sambrook, Fritsch and Maniatis (Cold Spring Harbor Laboratory Press: 2001); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Manipulating the Mouse Embryo, (Cold Spring Harbor Laboratory Press, Cold Spring Harbor, N.Y., 1986).

U.S. Patent Publication Nos. 2003/0219898, 2003/0148513, and 2003/0139410 are incorporated by reference to the extent they are not inconsistent with the teachings herein. The first two of these patent applications describe multiple uses of increased potency cells obtained from the taught methods, and in particular, the implantation of stem cells for different therapeutic treatments of neurological trauma and degenerative conditions. The third patent application is directed to the use of certain compounds to stimulate proliferation and migration of stem cells. Furthermore, U.S. Patent Publication Nos. 2006/0110440 and 2006/134789 are also incorporated by reference, which disclose methods of biasing differentiation of stem cells into specified neural cells. Those skilled in the art will readily appreciate that the cells of the present invention could be obtained, or their effectiveness enhanced, by combining with the teachings of the aforementioned patent applications, without undue experimentation.

The present invention is directed to compositions, methods and systems that provide for increased percentage of multipotent or potent stem cells to become committed, or predisposed, to differentiate to a desired end-stage differentiated eye-related cell. More particularly, the present invention utilizes the introduction into such a stem cell of a nucleic acid sequence comprising a developmental control gene.

The present invention advances the art by demonstrating the utility, in multipotent stem cells, of introducing for expression a nucleic acid sequence that comprises a desired developmental control gene. One example of such introducing is transfection by a vector comprising the nucleic acid sequence. After such introducing, the introduced developmental control gene is expressed in the cell (or its progeny), at least transiently. By so altering a multipotent stem cell, the present invention provides for more consistent differentiation to a desired functional cell type, such as a retinal cell. In doing so, this is believed to reduce known risks of this type of cell transplantation, such as the risk of tumor growth upon implantation of cells from pluripotent embryonic cell cultures.

Thus, in some embodiments the present invention is directed to biasing a multipotent cell such that the cell becomes programmed, or biased, to differentiate into a desired cell type under appropriate external conditions. This is done in some embodiments so that in a pre-implantation cell culture a greater percentage of cells are either pre-disposed to differentiate to and/or do differentiate to a desired cell type. More particularly, in certain embodiments of this biasing, the cell is transformed so it expresses a certain factor that biases the same cells to differentiate to a desired cell type upon a later implantation to a particular tissue in a living organism. In such embodiments, this improves a differentiation ratio so that a higher percentage of cells introduced into a particular cell medium, a tissue culture, or a living organism in a particular location differentiate into the end-stage differentiated cell type that is desired. Without being bound to a particular theory, this is believed to increase the probability of success and overall effectiveness, and to decrease the risks associated with implantation of cells obtained from embryonic stem cells or embryonic-cell-like cells.

Thus, at a minimum, developmental control genes that may be used in the present invention to transfect cells to bias those cells (or their progeny) to differentiate to a desired end-stage cell type, here that cell type being cholinergic neurons, include, but are not limited to [xx].

The following examples are provided to further disclose the genesis, operation, scope and uses of embodiments of the present invention. These examples are meant to be instructive, and illustrative, and not to be limiting as to the scope of invention as claimed herein. These examples are to be considered with the referred to drawings.

Thus, embodiments of the present method provide for improved approaches to obtain retinal, corneal or lens cells, or cell having characteristics of such cells (eye cells). Embodiments of the present invention provide a higher percentage of a population of cells biased, or disposed, to differentiate to one of the eye cell types The present invention may provide utility by biasing human neural stem cells through genetically manipulation so that the cells so manipulated may be used in research, including as cells transplantable, such as in experiments, and therapies, including regarding replacing damaged cholinergic neurons.

As to the efficiency of biasing to a desired cell type, and to observing cells having characteristics of a desired end-stage cell type, without being bound to a particular theory, it is believed that the factors that increase the efficiency of biasing by transfection include: 1) inherent properties of the cell to be transfected; 2) inherent efficiency of the selected vector or method of transfection; 3) relative percentage of cells in which the introduced nucleic acid sequence enters the nucleus compared to remains in the cytoplasm; and 4) number of copies of the nucleic acid sequence that are available for expression in the cell. Methods of transfection are well-known in the art, and the use and modification of known approaches to transfection of a cell with a nucleic acid sequence to be expressed therein to improve the percentage of biasing are within the scope of the present invention.

Thus, it is appreciated that in some embodiments of the present invention, a multipotent stem cell is transfected with a desired developmental control gene, and the expression of the gene during in vitro culture biases the differentiation of that cell to a desired end-stage differentiated cell. In other embodiments, the multipotent stem cell may be transfected in vivo with a developmental control gene whose expression biases transfected cells to differentiate into a desired end-stage cell. In any of such embodiments, accessory cells may provide factors that are needed for, or that assist with, the differentiation of the transfected cell. These accessory cells, such as the co-cultured LA-N-2 cells in the above example, need not be in contact with the transfected cells, demonstrating here that the factors are membrane permeable. These factors may include the same factor that is expressed by the transfected gene, or may be other factors known in the art or later determined to be useful in achieving a desired differentiation.

Also, it is appreciated that multipotent stem cells may be cultured without an accessory cell, and may receive factors by direct addition of factors to the culture medium, or such factors may be released by cells at a site of implantation, or may be added to a site of implantation.

Cell sorting technology is combined with the above-described embodiments of the present invention, particularly the vector embodiments, to improve the yield and selection of desired cells having the bias to differentiate to a desired end-stage cell (or having already so differentiated). For example, not to be limiting, the introduction of genetic marking such as described above, using EFGP, and the use of Fluorescent Activated Cell Sorter (FACS) techniques is utilized to sort and select cells that have been transfected with the desired developmental control gene (which is linked to a marker on the vector). The FACS technology is well known in the art (See, for example, U.S. patent application number 2002/0127715 A1.)

The above embodiments utilize specific sequences of genes incorporated into respective vectors and introduced into stem cells such as HNSCs or Mesenchymal stem cells. However, the present invention is not meant to be limited to the specifics of these examples. In a particular embodiment, sequences to Pax 6, Klf4 and Otx 2 are implemented. Examples of cDNA sequences, and corresponding translated polypeptide and protein sequences, of these and other developmental control genes are readily obtainable from the GenBank online database (See http://www.ncbi.nlm.nih.gov/entrez/query.fcgi.), and these are hereby incorporated by reference for that purpose.

Also, as to the nucleic acid sequences comprising the genes of interest, specific sequences of which are provided in the above examples and in the above paragraph, it is appreciated that substantial variation may exist in a nucleic acid sequence for a gene, yet a polypeptide or protein may nonetheless be produced in a cell from one of a number of such variant nucleic acid sequences, wherein such polypeptide or protein has a desired effect on the cell comparable to a polypeptide or protein produced from one of the nucleic acid sequences specified in the above examples. That is, variations may exist in a nucleic acid sequence for a gene yet the variations nonetheless function effectively when substituted for a nucleic acid sequence of a specified gene.

Accordingly, embodiments of the present invention also include and/or employ nucleic acid sequences that hybridize under stringent hybridization conditions (as defined herein) to all or a portion of a nucleic acid sequence represented by any of the SEQ ID Nos. 1, 2 or 3, (YY, ZY or AY, respectively, on attachments hereto), or their complements. The hybridizing portion of the hybridizing nucleic acid sequences is typically at least 15 (e.g., 20, 25, 30, or 50) nucleic acids in length. The hybridizing portion of the hybridizing nucleic acid sequence is at least 80%, e.g., at least 95%, or at least 98%, identical to the sequence of a portion or all of a nucleic acid sequence encoding one of genes identified by the noted Sequence ID numbers, or one of their complements. Hybridizing nucleic acids of the type described herein can be used, for example, as a cloning probe, a primer (e.g., a PCR primer), or a diagnostic probe, as well as for a gene transfected into a cell as described in the examples above.

Hybridization of the oligonucleic acid probe to a nucleic acid sample typically is performed under stringent conditions. Nucleic acid duplex or hybrid stability is expressed as the melting temperature or Tm, which is the temperature at which a probe dissociates from a target DNA. This melting temperature is used to define the required stringency conditions. If sequences are to be identified that are related and substantially identical to the probe, rather than identical, then it is useful to first establish the lowest temperature at which only homologous hybridization occurs with a particular concentration of salt (e.g., SSC or SSPE).

Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch. Stringent conditions involve hybridizing at 68° C. in 5×SSC/5×Denhardt's solution/1.0% SDS, and washing in 0.2×SSC/0.1% SDS at room temperature. Moderately stringent conditions include washing in 3×SSC at 42° C. The parameters of salt concentration and temperature can be varied to achieve the optimal level of identity between the probe and the target nucleic acid. Additional guidance regarding such conditions is readily available in the art, for example, by Sambrook et al., 1989, Molecular Cloning, A Laboratory Manual, Cold Spring Harbor Press, N.Y.; and Ausubel et al. (eds), 1995, Current Protocols in Molecular Biology, (John Wiley & Sons, N.Y.) at Unit 2.10.

The above-specified sequences are not meant to be limiting. For example, provided herein are additional identified sequences for relating to the Sequences 1, 2, and 3 may be used that are known and searchable via GenBank.

Further, the sequences for introduced genes and polypeptides or proteins expressed by them may also be defined in terms of homology to one of the sequences provided in the above examples and discussion. In the context of the present application, a nucleic acid sequence is "homologous" with the sequence according to the invention if at least 70%, preferably at least 80%, most preferably at least 90% of its base composition and base sequence corresponds to the sequence specified according to the invention. According to the invention, a "homologous protein" is to be understood to comprise proteins which contain an amino acid sequence at least 70% of which, preferably at least 80% of which, most preferably at least 90% of which, corresponds to the amino acid sequence disclosed in (Gish and States, 1993); wherein corresponds is to be understood to mean that the corresponding amino acids are either identical or are mutually homologous amino acids. The expression "homologous amino acids" denotes those which have corresponding properties, particularly with regard to their charge, hydrophobic character, steric properties, etc. Thus, a protein may be from 70% up to less than 100% homologous to any one of the proteins expressed by one of the disclosed introduced genes.

Homology, sequence similarity or sequence identity of nucleic acid or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Alternatively, as used herein, "percent homology" of two amino acid sequences or of two nucleic acids is determined using the algorithm of Karlin and Altschul (Proc. Natl. Acad. Sci. USA 87:2264-2268, 1990), modified as in Karlin and Altschul (Proc. Natl. Acad. Sci. USA 90:5873-5877, 1993). Such an algorithm is incorporated into the NBLAST and XBLAST programs of Altschul et al. (J. Mol. Biol. 215:403-410, 1990). BLAST nucleic acid searches are performed with the NBLAST program, score=100, wordlength=12, to obtain nucleic acid sequences homologous to a nucleic acid molecule of the invention. BLAST protein searches are performed with the XBLAST program, score=50, wordlength=3, to obtain amino acid sequences homologous to a reference polypeptide. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., XBLAST and NBLAST) are used. See http://www.ncbi.nlm.nih.gov.

Further, in addition to the homology, as indicated in certain claims (i.e., for some embodiments), is a requirement that the homologous or hybridizable nucleic acid sequence or polypeptide or protein functions analogously to the specified sequence of which it is homologous or with which it is hybridizable. That is, the homologous or hybridizable variant functions to achieve the same result, i.e., to increase the probability of a transfected cell, or the percentage of a number of cells, that are biased to differentiate to a cell, or cells, respectively, having characteristics of a desired end-stage differentiated cell.

While the transfection into HNSCs in the above examples uses the Neuroporter approach (Gene Therapy Systems, Inc. San Diego, Calif.), it is appreciated that any known or later-developed method of introduction of a nucleic acid sequence may be employed in the methods and systems, and to produce the compositions, of the present invention. For example, and not to be limiting, introduction of a nucleic acid sequence may be effectuated by stable or transient transfection, lipofection by methods other than Neuroporter, calcium phosphate treatment, electroporation, infection with a recombinant viral vector, and the use of vectors comprising a plasmid construct. Generally and collectively, these methods are considered to be included in the term "means to transfect," in the term "step for transfecting." Also, the use of the particular promoter and polyadenylation transcription termination site are not meant to be limiting, as many promoter and transcription termination sites are known and used routinely in the art.

As to the use of different means to transfect, and in view of the above discussion of the relative percentage of cells biased to cells having characteristics of a desired end-stage cell type, it is appreciated that types of transfection, cells that are transfected, and other factors, including post transfection conditions, affect the percentage of cells ultimately biased. In view of these factors, and considering the importance of the specific developmental control genes that are introduced to a cell in certain embodiments of the present invention, in some embodiments the percentage of transfected cells biased exceeds 40 percent, in other embodiments the percentage of transfected cells biased exceeds 50 percent, in other embodiments the percentage of transfected cells biased exceeds 65 percent, and in other embodiments the percentage of transfected cells biased exceeds 70 percent. However, it also is appreciated that determination of the percentage of cells that are in fact transfected in a given container of cells may be difficult to assess, the performance of the present invention in certain embodiments may be expressed in an alternative manner. That is, in some embodiments of the present invention in which a number of cells has been exposed to a selected method or means of transfection for the purpose of introducing a desired developmental control gene (such as Lhx8), the percentage of total cells that are biased to a desired end-stage cell type, or to a cell having characteristics of a desired end-stage cell type, is at least 35 percent, in other embodiments such percentage of total cells exceeds 50 percent, and in other embodiments such percentage of total cells exceeds 70 percent.

Further, it is appreciated that embodiments of the present invention are described as follows:

1. A neural stem cell, including a human neural stem cell, comprising an introduced nucleic acid sequence having an expressible developmental control gene, the expression of said gene being effective to increase the probability of differentiation of said cell to a desired neural cell type.
2. A neural stem cell, including a human neural stem cell, comprising an introduced nucleic acid sequence having an expressible developmental control gene, the expression of said gene being effective to increase the probability of differentiation of said cell to a cell having characteristics of a cholinergic neuron.
3. A neural stem cell, including a human neural stem cell, comprising an introduced nucleic acid sequence having an expressible developmental control gene, the expression of said gene being effective to increase the probability of differentiation of said cell to a cell having characteristics of an inner ear hair cell.
4. A neural stem cell, including a human neural stem cell, comprising an introduced nucleic acid sequence having an expressible developmental control gene, the expression of said gene being effective to increase the probability of differentiation of said cell to a cell having characteristics of a dopaminergic neuron.

Also, it is appreciated that the present invention, particularly for the genes Pax6, Klf4 or Otx2, may be utilized in potent cells, that is, in cells that are considered to fall within the definitions of pluripotent, of multipotent, and of progenitor cells (i.e., more differentiated than multipotent yet capable of limited self-renewal).

Based on the above examples and disclosure, in view of the knowledge and skill in the art, it also is appreciated that embodiments of the present invention also are used for any homeobox gene, so that a homeobox gene is transfected to a stem cell to effect a biasing of the stem cell to differentiate to a desired end-stage cell, or to a cell having characteristics of the end-stage cell. The stem cell may be a pluripotent or a multipotent stem cell; alternatively invention embodiments transfecting homeobox genes may be practiced with progenitor cells as described herein. Cells so biased by these genes following the methods of the present invention also are considered to fall within the scope of embodiments of the present invention.

EXAMPLE 1

Directed Differentiation of Adult Stem Cells Towards Retinal, Corneal and Lens Cells Functional blindness and lack of treatment options for corneal scaring and trachoma continue to be a growing problem throughout the world (Whitcher 2001). Cell replacement therapy is an attractive option but the ability to generate corneal cells remains a challenge (Daniels 2001). The utilization of factors involved in corneal development may provide a method for generating these cells in vitro for transplantation. Previous research has highlighted two important transcription factors, Pax6 and Klf4, which are important in development along with structural proteins that provide the physical properties of the cell. Using an approach of biasing cell differentiation using transcription factors, it is desired to generate corneal and lens cells from human mesenchymal stem cells in vitro. Human mesenchymal stem cells (MSCs) were selected given that corneal and lens tissue is mesoderm in origin. We propose that the forced expression of KLF4 and Pax6 in human mesenchymal cells will induce differentiation towards corneal and lens cells through the upregulation of functional proteins. This will provide a proof of concept to rapidly produce retinal, corneal and lens cells for further study or transplantation.

The experiments revealed that MSCs transfected with Pax6, Klf4, or both showed and increase in genes associated with ocular differentiation. Pax6 showed strong up-regulation after 1 week, but Klf4 was not detected. These results indicate that MSC transfection is transient with the gene being completely cleared in less than 1 week unless endogenous mechanisms are in place to maintain their expression. However, transient transfection was enough to up-regulate a number of genes that may be involved in a positive feedback mechanism that only initially required Klf4. Repeated trials suggest that Klf4 initiates expression, but extended culture requires additional factors to sustain expression. These results show to be promising because improved gene delivery and slightly modified culturing systems can be used to generate lens and corneal cells in vitro.

Retinal Introduction:

Blindness is estimated to affect 37 million people worldwide with an additional 124 million suffering from significant visual impairment. (Dandona 2006) Cell replacement therapy offers the potential to treat visual impairments such as retinal degeneration but cell procurement and proper differentiation has been a challenge. (Meyer 2005) The results of experimental transplantation of retinal photoreceptor cells have not been convincing, but persuading enough to demonstrate that transplantation may have beneficial results. Establishment of an efficient method of in vitro differentiation may serve as a starting point in selection treatment methods of transplanted cells. Proper differentiation needs to be established by examining expression of retinal progenitor cell markers such as Six3, Six6, NR2E3, NRL, CRX, and CHX10. (Akimoto 2005) Multiple transcription factors seem to be involved in retinal differentiation, but Pax6 and Otx2 have been shown to have an especially large impact.

Retinal development occurs through an orchestration of events dependant on transcription factors, cell signaling, and temporal regulation within a time-sensitive sequence of events. The inventors propose that a recapitulation of these developmental signals using human neural stem cells may facilitate retinal development in vitro. Specifically, we propose that utilization of certain hierarchal transcription factors is sufficient to initiate a developmental cascade to invoke retinal differentiation. It has been well established that genes encoding for Pax6 and Rx are important for the differentiation of retinal progenitor cells. (Ikeda 2005). In fact, knockout studies reveal that animals lacking Pax6 fail to undergo normal eye development. (Collinson 2003) Similarly, Otx2 also induces a photoreceptor-specific phenotype (Akagi). However, the direct causality of these genes in inducing retinal development has not been established. We propose that the forced expression of Pax6, Rx, and Otx2 in cells committed to neural differentiation will push the development towards retinal cells. Given the inability to clone Rx, we utilized a combination of Pax6 and Otx2 to induce retinal differentiation.

Corneal Introduction:

Functional blindness continues to be a growing problem throughout the world, particularly in developing countries where ocular infections receive inadequate treatment. (Whitcher 2001) Lack of treatment options to reverse damage resulting from trachoma and corneal scaring emphasize the need for corneal replacement therapy. (Daniels 2001) Additionally, the increase in the aging population translates to greater incidence of cataracts, and no functional lens equivalent exists. The cornea is a major structure of the ocular surface that is essential for vision and damage, such as from trauma, can scar the tissue causing functional blindness by preventing light from reaching the retina. Alterations of corneal processes such as proliferation, differentiation, adhesion, and extra cellular matrix homeostasis cause a deregulation of its integrity, which can induce various opthalmological pathologies. Cell replacement therapy is an attractive option but the ability to generate corneal cells remains a challenge. (Daniels 2001) The utilization of factors involved in corneal development may provide a method for generating these cells in vitro for transplantation. Previous research has highlighted two important transcription factors, Pax6 and Klf4, which are important in development along with structural proteins that provide the physical properties of the cell.

The continued presence of Pax6 in the adult corneal epithelium has been well established, but its role in this capacity is still very unclear (Sivak 2004). Pax6 knockout models result in a lack of development of the entire structure of the eye, therefore Pax6 is necessary for initial development. In order to study detailed analysis of its role, one study used Pax6 chimeras during embryonic development and found that Pax6 is required not only for the corneal epithelium, where it is expressed in high levels, but also the corneal stroma and endothelium, where this protein is detected at very low levels. Pax6 is also required for maintenance of lens competence. (Collinson 2003) The presence of KLF transcripts has been similarly verified. Specifically confirmed is the conservation of the biological properties of Klf4 in a corneal derived epithelial cell line (Chiambaretta 2004), and Klf4's influence on the up-regulation of other corneal genes like keratin-12 (Chiambaretta 2002).

Using an approach of biasing cell differentiation using transcription factors, we generated corneal and lens cells from human mesenchymal stem cells in vitro. Human mesenchymal stem cells were selected given that corneal and lens tissue is mesoderm in origin. Similarly, we propose that the forced expression of KLF4 and Pax6, two transcription factors expressed early in corneal differentiation, in human mesenchymal cells will induce differentiation towards corneal and lens cells through the upregulation of functional proteins. This will provide a proof of concept to rapidly produce retinal, corneal and lens cells for further study or transplantation.

Methods:

Genes were chosen by identifying specific transcription factors relating to retinal, corneal, and lens cells. Primers were then designed using the Invitrogen and Oligo 6.8 programs. The criteria used to design each primer includes:
1. PCR Product length between 100-500, optimally set for 100-200 base pairs
2. Duplex formation has to have energy values greater than −5 kcal/mol between the forward-forward primers, reverse-reverse primers, and forward-reverse primers
3. Temperature difference no more than 3° between the forward and reverse primers
4. Hairpin formation no greater than 3 nucleotide base pairs
5. False-priming sites below a threshold of 180

Retinal primers made include Six3, Otx2, Chx10, FoxE3, NR2E3, Six6, NRL, Hes3 and CRX. Corneal and lens primers made include CRYAA, TRPC4, KLF4, LAMA5, IVL and ITBG1. Pax6 was made and shared between the experiments.

The optimum temperature of each primer was determined by running PCR on a temperature gradient using the Hotmaster mix protocol. The gradient consisted of 52° C., 52.8° C., 54° C., 55.7° C., 58.2° C., 60.1° C., 61.3° C., and 62° C. Gel electrophoresis was performed and the optimum temperature was found by judging the band size for each primer. Some primers required repeated trials using genomic DNA instead of cDNA; due to inconclusive results, Real-Time PCR using a temperature gradient was performed on all the primers. Additionally, other primers involved in embryonic stem cells and inner ear hair cells were optimized within the RT-PCR gradient. This yielded the optimum temperatures as described in the Table 1 below.

TABLE 1

| Temp ° C. | Eye primers | Angel's primers |
| --- | --- | --- |
| 52 | Hes3, Chx10, NR2E3, IVL | Activin, BarhL1, Pou4F3, Delta1, Calretinin, PDCH15 |
| 52.8 | — | Terf1, FoxD3, Myosin7A |
| 54 | TRPC4, Six6 | Notch |
| 55.7 | Rx, ITBG1, CRX | — |
| 58.2 | NRL, KLF4, Pax6 | Rex1, Oct34, Nanog, Sox2, Hath1 |
| 60.1 | Otx2, Six3 | Ink4D |
| 61.3 | Hes1, CRYAA, LAMA5, GAPDH, FoxE3 | Cripto, CDH23, Hes5 |
| 62 | — | BMPR1A |

Following temperature optimization, gel electrophoresis was performed to ensure product quality and length. Primer efficiency was calculated by running all primers through a cDNA concentration gradient on Real-Time PCR following the manufacturer's SYBR Green protocol. 12.5 µL of iQ SYBR Green Supermix, 0.6 µL of Forward Primer, 0.6 µL of Reverse Primer, 1 ug of DNA template, and Molecular Biology Grade water all combined to form a Reaction Set Up total volume of 30 µL. The first trial used a concentration gradient of 1:1, 1:¼, 1:¹⁄₁₆, and 1:¹⁄₆₄ on a temperature gradient to account for the varying optimum temperatures of the many primers. These results were inconclusive due to pipetting error associated with such small volumes of cDNA. A second trial was performed using a concentration gradient of 2:1, 1:1, 1:½, and 1:¼. To calculate efficiency, the log of the concentrations of the dilutions of DNA was plotted against the Threshold Cycle. The efficiency was found using the equation $E = 10^{-(1/slope)}$. Due to unreal results, the experiment had to be repeated again, and it was advised that the RT-PCR trials should be ran using one temperature for the whole plate. The third trial consisted of primers that had the optimum temperature of 61.3° C. The fourth and fifth trials were conducted at 52° C. and 58.2° C. respectively. In the last trial, a mixture of frosted-capped microtubes and clear-capped microtubes were used, leading to inconclusive results for many of the primers. The efficiencies were calculated, with the results as provided in Table 2 below.

TABLE 2

| Primers (61.3° C.) | Efficiency | Primers (52° C.) | Efficiency | Primers (58.2° C.) | Efficiency |
|---|---|---|---|---|---|
| Hes1 | 2.009 | IVL | 2.207 | NRL | 1.928 |
| GAPDH | 2.116 | Delta1 | 1.779 | Pax6 | 1.604 |
| LAMA5 | 2.169 | Pou4F3 | 2.670 | KLF4 | — |
| CRYAA | 1.759 | PDH25 | 2.091 | Hath1 | 2.098 |
| FoxE3 | 1.820 | NR2E3 | 2.123 | Nanog | 2.417 |
| CDH23 | 1.727 | BarhL1 | — | Oct4 | — |
| Cripto | — | Chx10 | 2.219 | Rex1 | — |
| Hes5 | 1.498 | Hes3 | 3.195 | Sox2 | — |

YFP, pmaxGFP, Otx2, Pax6, and KLF4 were purified using an endotoxin-free affinity column plasmid purification kit according to manufactures' protocol. Briefly, a lysis step was performed following resuspension of the bacterial pellets in buffers S1, S2, S3. The lysate was centrifuged and filtered to clear flocculent and debris. The cleared lysate was then equilibrated using buffer N2 and washed through an affinity column with buffers N3 and N4. The DNA was eluted with buffer N5 and collected in an endotoxin free tube. The isolated DNA was precipitated with isopropanol and then centrifuged. Following centrifugation, the DNA pellet was washed with 70% ice-cold endotoxin-free ethanol. The wash was repeated, subsequently, the ethanol was removed and the pellet was redissolved in Molecular Biology Grade water. Plasmid yields were determined by UV spectrophotometry and an enzyme digestion was performed to ensure product quality (see Table 3). Following unexpected band patterns, the samples were sent for DNA analysis which confirmed the contamination of foreign DNA. New vectors were received, purification was performed, and DNA analysis confirmed pure results.

TABLE 3

| Gene | Concentration [μG/μL] | $A_{260/280}$ |
|---|---|---|
| YFP | 0.050 | — |
| Pmax GFP | 0.169 | — |
| Otx2 | 0.172 | — |
| KLF4$_1$ | 0.626 | 2.399 |
| KLF4$_2$ | 0.859 | 2.196 |
| Pax6$_1$ | 0.641 | 1.841 |
| Pax6$_2$ | 0.583 | 1.825 |

Retinal gene expression was forced by chemically transfecting NT2 cells with Pax6, Otx2 and combinations of both genes. Lipofectamine protocol was slightly altered from the manufacture's recommendations. Trials were conducted with 100,000 or 50,000 cells per well in a 6-well plate. All wells, including the controls, received a Lipofectamine dilution of 6 μL transfection reagent in 54 mL serum-free OptiMEM medium. The variable wells received a total of 1.5 μg DNA diluted in 50 μL OptiMEM medium, while the controls' "DNA" dilution contained only OptiMEM. The 50 μL aliquots were combined and reagent-DNA complexes were allowed to form for 20 minutes before being added to each well. Cell medium was changed 24 hours post-transfection and every three to four days thereafter. Samples were analyzed at 1 week, 2 weeks, or 1 month post-transfection.

Corneal and lens gene expression was forced using both chemical and electroporation transfection methods. Chemical transfection followed the Fugene protocol with slight modifications to the manufacturers recommendations. 50,000-100,000 cells were transfected using 9 μL of Fugene, 3 ug of DNA and αMEM media. The control cells were given just Fugene with pmaxGFP. The transfected cells were then distributed drop by drop over the area of a well already containing 2 ml of αMEM media.

Electroporation protocol was followed when forcing gene expression electrically. In a total volume of 200 μL, 50,000-100,000 cells were transfected with 3 ug of DNA and alpha-MEM media. They were transfected at 600V with a pulse length of 0.10 s in a 2 mm cuvette. 500 μL of OptiMEM media, a low calcium media, was added to the transfected cells and incubated for 10 minutes. The cell solution in the cuvette was transferred using a pipette and expelled drop my drop over the area of a well already containing 2 ml of αMEM media. All transfected cells were incubated for a period of 1 week, 2 weeks, or 1 month. RNA extraction was then performed on the samples followed by cDNA synthesis.

The Invitrogen RNA extraction protocol was followed as per the manufacturer's recommendations. Cells grown in monolayer were homogenized by lysis with TRIzol Reagent and combined with 20% addition of chloroform for phase separation. The RNA was precipitated by isopropyl alcohol and washed with ethanol. The supernatant was carefully removed and the RNA pellet was dried and redissolved in Molecular Biology Grade water. The concentrations were determined by a UV spectrophotometer.

cDNA synthesis was performed on the isolated RNA according to the manufacturer's specifications. The iScript cDNA Synthesis protocol includes 8 μL of 5× iScript Reaction Mix, 2 μL of iScript Reverse Transcriptase, and 1-2 μg of RNA, brought to a volume of 40 μL with Molecular Biology Grade water. PCR was allowed to run for 30 cycles to increase the quantity of cDNA. The concentrations were then determined using UV spectrophotometry.

Results and Conclusion:

NT-2 cells were transfected with Otx2 and Pax6 and cultured for one week. Media was changed one day post-transfection, and changed every three days thereafter. One week

| RT-PCR Data: 61204 hNSC Pax6-Otx2 Lipofectamine transfected | |
|---|---|
| Genes | Relative Gene Expression |
| FoxE3 | 6.2 |
| Otx2 | 1.2 E7 |
| NRL | 0.48 |
| Pax6 | 1.3 E6 |
| Klf4 | 1.2 |
| bActin | 1 |
| Six6 | 0.48 | post-transfection, cells were lysed and cDNA was produced. Upon screening with the primers, it was found that only FoxE3 was upregulated. Unexpectedly, Pax6 and Otx2 were not detected at one week, indicating either poor transfection or, more likely, rapid clearing of the transiently transfection genes. Interestingly, many of the genes were not expressed at all. It was hypothesized that the NT-2 cells were too immature to be able to be responsive to the transcription factors delivered to the cells. This idea is supported by the original optimization experiments, where gene expression was observed in cDNA samples derived from retinoic acid treated NT-2 cells. For that reason, the experiments were repeated using neural stem cells. The NSC cDNA derived from 1 month post-transfection of Pax6 and Otx2 showed upregulation of FoxE3, Otx2, and Pax6 (Table 4). These results show that Otx2 and Pax6 expression is maintained in NSC's for up to one month, but not in NT-2 cells. Additionally, more genes might be upregulated, but since a low concentration of DNA was used initially, only highly expressed genes are likely to be detected in the RT-PCR. These results indicate that Otx2 and Pax6 may be sufficient to increase some genes involved with retinal differentiation, but other factors are critical for proper retinal differentiation. Specifically, the addition of growth factors and retinoic acid in NSC's may show more dramatic differentiation.

MSCs transfected with Pax6, Klf4, or both showed and increase in genes associated with ocular differentiation. In particular, CRYAA, LAMA5, IVL, and Pax6 showed strong up-regulation after 1 week, but Klf4 was not detected. These results indicate that MSC transfection is transient with the gene being completely cleared in less than 1 week unless endogenous mechanisms are in place to maintain their expression. However, transient transfection was enough to up-regulate a number of genes that may be involved in a positive feedback mechanism that only initially required Klf4. A repeated trial of 2 weeks post-transfected MSCs with Pax6 and KLF4 showed up-regulation of LAMA5, IVL, and ITBG1, but interestingly, CRYAA and Pax6 were not detected. See Table 5. These results suggest that Klf4 initiates expression, but extended culture requires additional factors to sustain expression. Additionally, in the 2-week transfected MSCs, all of the wells contained clusters, but one well had a large aggregation of clusters.

TABLE 5

| Genes | 61120 hMSC 1w Pax6-Klf4 Ept Relative Gene Expression | 61204 hMSC 2w Pax6-Klf4 Ept Relative Gene Expression |
|---|---|---|
| Otx2 | 4.0 E5 | 0.52 |
| Pax6 | 1.9 E3 | |
| Klf4 | 0.12 | |
| bActin | 1.0 | 1.0 |
| LAMA5 | 18.1 | 3.6 |
| CRYAA | 8.5 | |
| ITBG1 | 0.90 | 1.6 |
| TRPC4 | 1.1 | 1.1 |
| IVL | 2.6 | 8.0 |

CONCLUSION

In NT2 cells, gene expression of Pax6 and Otx2 did not persist beyond a few days. Despite persistent gene expression in hNSC, only FoxE3 was up-regulated. This data suggests that additional growth factors may be required, such as FGF2.

Klf4 and Pax6 up-regulates corneal and lens cell genes however vector-induced expression only persists for a few days. Interestingly, transient expression of Klf4 is enough to up-regulate other genes despite the fact that it is not present at 1 w. These results indicate that gene expression and/or gene silencing of the identified genes may be sufficient to generate lens and corneal cells in vitro.

REFERENCES

Akimoto M., Transcriptional Factors Involved in Photoreceptor Differentiation. Semin Opthalmol. 2005 Jan.-Mar.; 20(1):25-30.

Akagi T, Mandai M, Ooto S, Hirami Y, Osakada F, Kageyama R, Yoshimura N, Takahashi M. Otx2 homeobox gene induces photoreceptor-specific phenotypes in cells derived from adult iris and ciliary tissue. Invest Opthalmol Vis Sci. 2004 December; 45(12):4570-5.

Chiambaretta F, Blanchon L, Rabier B, Kao W W, Liu J J, Dastugue B, Rigal D, Sapin V., Regulation of Corneal Keratin-12 Gene Expression by the Human Kruppel-like Transcription Factor 6. Invest Opthalmol Vis Sci. 2002 November; 43(11):3422-9.

Chiambaretta F, De Graeve F, Turet G, Marceau G, Gain P, Dastugue B, Rigal D, Sapin V. Cell and tissue specific expression of human Kruppel-like transcription factors in human ocular surface. Mol Vis. 2004 Nov. 23; 10:901-9.

Collinson J M, Quinn J C, Hill R E, West J D., The roles of Pax6 in the Cornea, Retina, and Olfactory Epithelium of the Developing Mouse Embryo. Dev Biol. 2003 Mar. 15; 255(2):303-12.

Dandona L, Dandona R. What is the global burden of visual impairment? BMC Med. 2006 Mar. 16; 4:6. Review.

Daniels J T, Dart J K, Tuft S J, Khaw P T. Corneal stem cells in review. Wound Repair Regen. 2001 Nov.-Dec.; 9(6): 483-94.

Ikeda H, Osakada F, Watanabe K, Mizuseki K, Haraguchi T, Miyoshi H, Kamiya D, Honda Y, Sasai N, Yoshimura N, Takahashi M, Sasai Y. Generation of Rx+/Pax6+ neural retinal precursors from embryonic stem cells. Proc Natl Acad Sci USA. 2005 Aug. 9; 102(32):11331-6. Epub 2005 Aug. 2.

Meyer J S, Katz M L, Kirk M D. Stem cells for retinal degenerative disorders. Ann N Y Acad Sci. 2005 May; 1049:135-45

Sivak J M, West-Mays J A, Yee A, Williams T, Fini M E., Transcription Factors Pax6 and AP-2alpha Interact To Coordinate Corneal Epithelial Repair by Controlling Expression of Matrix Metalloproteinase Gelatinase B. Mol Cell Biol. 2004 Jan.; 24(1):245-57.

Whitcher J P, Srinivasan M, Upadhyay M P. Corneal blindness: a global perspective. Bull World Health Organ. 2001; 79(3): 214-21.

Further, and more generally, embodiments of the present invention may be practiced by transfecting a stem or a progenitor cell with a nucleic acid sequence comprising a development control gene, so that the transfecting is effective to bias the cell to differentiate to a desired end-stage cell, or to a cell having characteristics of the end-stage cell.

Also, it is appreciated that the methods of the present invention may be applied to the daughter cells of multipotent cells, which may have begun some stages of differentiation but are still capable of being biased by transfection of appropriate developmental control genes as described herein, but by virtue of initiating differentiation (or being less self-renewing) may by some opinions therefore not be considered to be multipotent cells. For the purposes of this invention, such daughter cells, which may be found in culture with the multipotent stem cells from which they arose, are termed "biasable progeny cells."

It is appreciated that embodiments of the present invention also may be defined and claimed with regard to the polypeptide or protein sequences expressed as a result of the transfections disclosed and discussed above. For example, not to be limiting, the peptide sequences, disclosed as the translation sequences in the attached Sequence Listing pages, and their expression in a transfected cell, are used to identify and/or characterize a characteristic and/or result of embodiments of the present invention. Translation sequences are obtainable from the respective GenBank database data entries for cDNAs as described herein, and those database entries are incorporated by reference for such information.

While a number of embodiments of the present invention have been shown and described herein in the present context, such embodiments are provided by way of example only, and not of limitation. Numerous variations, changes and substitutions will occur to those of skilled in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A method of modifying a mesenchymal stem cell to up-regulate expression of CRYAA, LAMA5, IVL, or ITBG1 in said mesenchymal stem cell, in vitro, said method comprising the steps of: introducing a Pax 6 or Klf4 gene sequence, or a combination thereof, into said mesenchymal stem cell to produce a modified mesenchymal stem cell; and growing said modified mesenchymal stem cell under conditions to allow expression of said gene sequence or combination thereof, wherein expression of said gene sequence up-regulates expression of CRYAA, LAMA5, IVL and ITBG1 in said modified mesenchymal stem cell, in vitro.

* * * * *

SEQUENCE LISTING

```
<160> NUMBER OF SEQ ID NOS: 6

<210> SEQ ID NO 1
<211> LENGTH: 1399
<212> TYPE: DNA
<213> ORGANISM: Homo sapiens

<400> SEQUENCE: 1 aggggggaaga ctttaactag gggcgcgcag atgtgtgagg cctttattg tgagagtgga      60 cagacatccg agatttcaga gccccatatt cgagccccgt ggaatcccgc ggcccccagc    120
cagagccagc atgcagaaca gtcacagcgg agtgaatcag ctcggtggtg tctttgtcaa    180
cgggcggcca ctgccggact ccacccggca gaagattgta gagctagctc acagcggggc    240
ccggccgtgc gacatttccc gaattctgca ggtgtccaac ggatgtgtga gtaaaattct    300
gggcaggtat tacgagactg gctccatcag acccagggca atcggtggta gtaaaccgag    360
agtagcgact ccagaagttg taagcaaaat agcccagtat aagcgggagt gcccgtccat    420
ctttgcttgg gaaatccgag acagattact gtccgagggg gtctgtacca acgataacat    480
accaagcgtg tcatcaataa acagagttct tcgcaacctg gctagcgaaa agcaacagat    540
gggcgcagac ggcatgtatg ataaactaag gatgttgaac gggcagaccg gaagctgggg    600 cacccgcct ggttggtatc cggggacttc ggtgccaggg caacctacgc aagatggctg    660
ccagcaacag gaaggagggg gagagaatac caactccatc agttccaacg gagaagattc    720
agatgaggct caaatgcgac ttcagctgaa gcggaagctg caaagaaata aacatcctt    780 tacccaagag caaattgagg ccctggagaa agagtttgag agaacccatt atccagatgt    840
gtttgcccga gaaagactag cagccaaaat agatctacct gaagcaagaa tacaggtatg    900
gttttctaat cgaagggcca aatggagaag agaagaaaaa ctgaggaatc agagaagaca    960
ggccagcaac acacctagtc atattcctat cagcagtagt ttcagcacca gtgtctacca   1020
accaattcca caacccacca caccggtttc ctccttcaca tctggctcca tgttgggccg   1080
aacagacaca gccctcacaa acacctacag cgctctgccg cctatgccca gcttcaccat   1140
ggcaaataac ctgcctatgc aaccccagt ccccagccag acctcctcat actcctgcat   1200
gctgcccacc agcccttcgg tgaatgggcg gagttatgat acctacaccc ccccacatat   1260
gcagacacac atgaacagtc agccaatggg cacctcgggc accacttcaa caggactcat   1320
ttcccctggt gtgtcagttc cagttcaagt tcccggaagt gaacctgata tgtctcaata   1380
ctggccaaga ttacagtaa                                                1399

<210> SEQ ID NO 2
<211> LENGTH: 2488
<212> TYPE: DNA
<213> ORGANISM: Homo sapiens

<400> SEQUENCE: 2
ctcggccaat ttggggtttt gggttttggc ttcgtttctt ctcttcgttg actttgggt      60 tcaggtgccc cagctgcttc gggctgccga ggaccttctg gccccccaca ttaatgaggc   120
agccacctgg cgagtctgac atggctgtca gcgacgcgct gctcccatct ttctccacgt   180
```

```
tcgcgtctgg cccggcggga agggagaaga cactgcgtca agcaggtgcc ccgaataacc    240
gctggcggga ggagctctcc cacatgaagc gacttccccc agtgcttccc ggccgcccct    300
atgacctggc ggcggcgacc gtggccacag acctggagag cggcggagcc ggtgcggctt    360
gcggcggtag caacctggcg cccctacctc ggagagagac cgaggagttc aacgatctcc    420
tggacctgga ctttattctc tccaattcgc tgacccatcc tccggagtca gtggccgcca    480
ccgtgtcctc gtcagcgtca gcctcctctt cgtcgtcgcc gtcgagcagc ggccctgcca    540
gcgcgccctc cacctgcagc ttcacctatc cgatccgggc cgggaacgac ccgggcgtgg    600
cgccgggcgg cacgggcgga ggcctcctct atggcaggga gtccgctccc cctccgacgg    660
ctcccttcaa cctggcggac atcaacgacg tgagccccctc gggcggcttc gtggccgagc    720
tcctgcggcc agaattggac ccggtgtaca ttccgccgca gcagccgcag ccgccaggtg    780
gcgggctgat gggcaagttc gtgctgaagg cgtcgctgag cgcccctggc agcgagtacg    840
gcagcccgtc ggtcatcagc gtcagcaaag gcagccctga cggcagccac ccggtggtgg    900
tggcgcccta caacggcggg ccgccgcgca cgtgccccaa gatcaagcag gaggcggtct    960
cttcgtgcac ccacttgggc gctggacccc ctctcagcaa tggccaccgg ccggctgcac   1020
acgacttccc cctggggcgg cagctcccca gcaggactac cccgaccctg ggtcttgagg   1080
aagtgctgag cagcagggac tgtcaccctg ccctgccgct tcctcccggc ttccatcccc   1140
acccggggcc caattaccca tccttcctgc ccgatcagat gcagccgcaa gtcccgccgc   1200
tccattacca agagctcatg ccacccggtt cctgcatgcc agaggagccc aagccaaaga   1260
ggggaagacg atcgtggccc cggaaaagga ccgccaccca cacttgtgat tacgcgggct   1320
gcggcaaaac ctacacaaag agttcccatc tcaaggcaca cctgcgaacc cacacaggtg   1380
agaaacctta ccactgtgac tgggacggct gtggatggaa attcgcccgc tcagatgaac   1440
tgaccaggca ctaccgtaaa cacacggggc accgcccgtt ccagtgccaa aaatgcgacc   1500
gagcattttc caggtcggac cacctcgcct tacacatgaa gaggcatttt taaatcccag   1560
acagtggata tgacccacac tgccagaaga gaattcagta ttttttactt ttcacactgt   1620
cttcccgatg agggaaggag cccagccaga aagcactaca atcatggtca agttcccaac   1680
tgagtcatct tgtgagtgga taatcaggaa aaatgaggaa tccaaaagac aaaaatcaaa   1740
gaacagatgg gatctgtgac tggatcttct atcattccaa ttctaaatcc gacttgaata   1800
ttcctggact acaaaatgc caaggggtg actggaagtt gtggatatca gggtataaat    1860
tatatctgtg agttggggga gggaagacca gaattccctt gaattgtgta ttgatgcaat   1920
ataagcataa aagatcacct tgtattctct ttaccttcta aaagccatta ttatgatgtt   1980
agaagaagag gaagaaattc aggtacagaa aacatgtttta aatagcctaa atgatggtgc   2040
ttggtgagtc ttggttctaa aggtaccaaa caaggaagcc aaagttttca aactgctgca   2100
tactttgaca aggaaaatct atatttgtct tccgatcaac attttatgacc taagtcaggt   2160
aatatacctg gtttacttct ttagcatttt tatgcagaca gtctgttatg cactgtggtt   2220
tcagatgtgc aataatttgt acaatggttt attcccaagt atgccttaag cagaacaaat   2280
gtgttttcct atatagttcc ttgccttaat aaatatgtaa tataaattta agcaaacgtc   2340
tattttgtat atttgtaaac tacaaagtaa aatgaacatt tgtggagtt tgtattttgc    2400
atactcaagg tgagaattaa gttttaaata aacctataat attttatctt aaaaaaaaaa   2460
aaaaaaaaaa aaaaaaaaa aaaaaaaa                                       2488
```

<210> SEQ ID NO 3
<211> LENGTH: 870
<212> TYPE: DNA
<213> ORGANISM: Homo sapiens

<400> SEQUENCE: 3

```
atgatgtctt atcttaagca accgccttac gcagtcaatg ggctgagtct gaccacttcg     60
ggtatggact tgctgcaccc ctccgtgggc tacccggcca ccccccggaa acagcgccgg    120
gagaggacga cgttcactcg ggcgcagcta gatgtgctgg aagcactgtt tgccaagacc    180
cggtacccag acatcttcat gcgagaggag gtggcactga aaatcaactt gcccgagtcg    240
agggtgcagg tatggtttaa gaatcgaaga gctaagtgcc gccaacaaca gcaacaacag    300
cagaatggag gtcagaacaa agtgagacct gccaaaaaga agacatctcc agctcgggaa    360
gtgagttcag agagtggaac aagtggccaa ttcactcccc cctctagcac ctcagtcccg    420
accattgcca gcagcagtgc tcctgtgtct atctggagcc cagcttccat ctccccactg    480
tcagatccct tgtccacctc ctcttcctgc atgcagaggt cctatcccat gacctatact    540
caggcttcag gttatagtca aggatatgct ggctcaactt cctactttgg gggcatggac    600
tgtggatcat atttgacccc tatgcatcac cagcttcccg accagggggc cacactcagt    660
cccatgggta ccaatgcagt caccagccat ctcaatcagt ccccagcttc tctttccacc    720
caaggatatg gagcttcaag cttgggtttt aactcaacca ctgattgctt ggattataag    780
gaccaaactg cctcctggaa gcttaacttc aatgctgact gcttggatta taaagatcag    840
acatcctcgt ggaaattcca ggttttgtga                                     870
```

<210> SEQ ID NO 4
<211> LENGTH: 422
<212> TYPE: PRT
<213> ORGANISM: Homo sapiens

<400> SEQUENCE: 4

```
Met Gln Asn Ser His Ser Gly Val Asn Gln Leu Gly Gly Val Phe Val
  1               5                  10                  15

Asn Gly Arg Pro Leu Pro Asp Ser Thr Arg Gln Lys Ile Val Glu Leu
             20                  25                  30

Ala His Ser Gly Ala Arg Pro Cys Asp Ile Ser Arg Ile Leu Gln Val
         35                  40                  45

Ser Asn Gly Cys Val Ser Lys Ile Leu Gly Arg Tyr Tyr Glu Thr Gly
     50                  55                  60

Ser Ile Arg Pro Arg Ala Ile Gly Gly Ser Lys Pro Arg Val Ala Thr
 65                  70                  75                  80

Pro Glu Val Val Ser Lys Ile Ala Gln Tyr Lys Arg Glu Cys Pro Ser
                 85                  90                  95

Ile Phe Ala Trp Glu Ile Arg Asp Arg Leu Leu Ser Glu Gly Val Cys
            100                 105                 110

Thr Asn Asp Asn Ile Pro Ser Val Ser Ser Ile Asn Arg Val Leu Arg
        115                 120                 125

Asn Leu Ala Ser Glu Lys Gln Gln Met Gly Ala Asp Gly Met Tyr Asp
    130                 135                 140

Lys Leu Arg Met Leu Asn Gly Gln Thr Gly Ser Trp Gly Thr Arg Pro
145                 150                 155                 160

Gly Trp Tyr Pro Gly Thr Ser Val Pro Gly Gln Pro Thr Gln Asp Gly
                165                 170                 175
```

```
Cys Gln Gln Gln Glu Gly Gly Gly Glu Asn Thr Asn Ser Ile Ser Ser
            180                 185                 190

Asn Gly Glu Asp Ser Asp Glu Ala Gln Met Arg Leu Gln Leu Lys Arg
        195                 200                 205

Lys Leu Gln Arg Asn Arg Thr Ser Phe Thr Gln Glu Gln Ile Glu Ala
    210                 215                 220

Leu Glu Lys Glu Phe Glu Arg Thr His Tyr Pro Asp Val Phe Ala Arg
225                 230                 235                 240

Glu Arg Leu Ala Ala Lys Ile Asp Leu Pro Glu Ala Arg Ile Gln Val
                245                 250                 255

Trp Phe Ser Asn Arg Arg Ala Lys Trp Arg Arg Glu Glu Lys Leu Arg
            260                 265                 270

Asn Gln Arg Arg Gln Ala Ser Asn Thr Pro Ser His Ile Pro Ile Ser
        275                 280                 285

Ser Ser Phe Ser Thr Ser Val Tyr Gln Pro Ile Pro Gln Pro Thr Thr
    290                 295                 300

Pro Val Ser Ser Phe Thr Ser Gly Ser Met Leu Gly Arg Thr Asp Thr
305                 310                 315                 320

Ala Leu Thr Asn Thr Tyr Ser Ala Leu Pro Pro Met Pro Ser Phe Thr
                325                 330                 335

Met Ala Asn Asn Leu Pro Met Gln Pro Pro Val Pro Ser Gln Thr Ser
            340                 345                 350

Ser Tyr Ser Cys Met Leu Pro Thr Ser Pro Ser Val Asn Gly Arg Ser
        355                 360                 365

Tyr Asp Thr Tyr Thr Pro Pro His Met Gln Thr His Met Asn Ser Gln
    370                 375                 380

Pro Met Gly Thr Ser Gly Thr Thr Ser Thr Gly Leu Ile Ser Pro Gly
385                 390                 395                 400

Val Ser Val Pro Val Gln Val Pro Gly Ser Glu Pro Asp Met Ser Gln
                405                 410                 415

Tyr Trp Pro Arg Leu Gln
            420

<210> SEQ ID NO 5
<211> LENGTH: 470
<212> TYPE: PRT
<213> ORGANISM: Homo sapiens

<400> SEQUENCE: 5

Met Ala Val Ser Asp Ala Leu Leu Pro Ser Phe Ser Thr Phe Ala Ser
1               5                   10                  15

Gly Pro Ala Gly Arg Glu Lys Thr Leu Arg Gln Ala Gly Ala Pro Asn
            20                  25                  30

Asn Arg Trp Arg Glu Glu Leu Ser His Met Lys Arg Leu Pro Pro Val
        35                  40                  45

Leu Pro Gly Arg Pro Tyr Asp Leu Ala Ala Thr Val Ala Thr Asp
    50                  55                  60

Leu Glu Ser Gly Gly Ala Gly Ala Ala Cys Gly Gly Ser Asn Leu Ala
65                  70                  75                  80

Pro Leu Pro Arg Arg Glu Thr Glu Glu Phe Asn Asp Leu Leu Asp Leu
                85                  90                  95

Asp Phe Ile Leu Ser Asn Ser Leu Thr His Pro Pro Glu Ser Val Ala
            100                 105                 110

Ala Thr Val Ser Ser Ser Ala Ser Ala Ser Ser Ser Ser Ser Pro Ser
        115                 120                 125
```

```
Ser Ser Gly Pro Ala Ser Ala Pro Ser Thr Cys Ser Phe Thr Tyr Pro
    130                 135                 140

Ile Arg Ala Gly Asn Asp Pro Gly Val Ala Pro Gly Gly Thr Gly Gly
145                 150                 155                 160

Gly Leu Leu Tyr Gly Arg Glu Ser Ala Pro Pro Thr Ala Pro Phe
                165                 170                 175

Asn Leu Ala Asp Ile Asn Asp Val Ser Pro Ser Gly Gly Phe Val Ala
                180                 185                 190

Glu Leu Leu Arg Pro Glu Leu Asp Pro Val Tyr Ile Pro Pro Gln Gln
            195                 200                 205

Pro Gln Pro Pro Gly Gly Gly Leu Met Gly Lys Phe Val Leu Lys Ala
        210                 215                 220

Ser Leu Ser Ala Pro Gly Ser Glu Tyr Gly Ser Pro Ser Val Ile Ser
225                 230                 235                 240

Val Ser Lys Gly Ser Pro Asp Gly Ser His Pro Val Val Ala Pro
                245                 250                 255

Tyr Asn Gly Gly Pro Pro Arg Thr Cys Pro Lys Ile Lys Gln Glu Ala
                260                 265                 270

Val Ser Ser Cys Thr His Leu Gly Ala Gly Pro Pro Leu Ser Asn Gly
                275                 280                 285

His Arg Pro Ala Ala His Asp Phe Pro Leu Gly Arg Gln Leu Pro Ser
    290                 295                 300

Arg Thr Thr Pro Thr Leu Gly Leu Glu Glu Val Leu Ser Ser Arg Asp
305                 310                 315                 320

Cys His Pro Ala Leu Pro Leu Pro Pro Gly Phe His Pro His Pro Gly
                325                 330                 335

Pro Asn Tyr Pro Ser Phe Leu Pro Asp Gln Met Gln Pro Gln Val Pro
                340                 345                 350

Pro Leu His Tyr Gln Glu Leu Met Pro Pro Gly Ser Cys Met Pro Glu
            355                 360                 365

Glu Pro Lys Pro Lys Arg Gly Arg Arg Ser Trp Pro Arg Lys Arg Thr
        370                 375                 380

Ala Thr His Thr Cys Asp Tyr Ala Gly Cys Gly Lys Thr Tyr Thr Lys
385                 390                 395                 400

Ser Ser His Leu Lys Ala His Leu Arg Thr His Thr Gly Glu Lys Pro
                405                 410                 415

Tyr His Cys Asp Trp Asp Gly Cys Gly Trp Lys Phe Ala Arg Ser Asp
                420                 425                 430

Glu Leu Thr Arg His Tyr Arg Lys His Thr Gly His Arg Pro Phe Gln
            435                 440                 445

Cys Gln Lys Cys Asp Arg Ala Phe Ser Arg Ser Asp His Leu Ala Leu
        450                 455                 460

His Met Lys Arg His Phe
465                 470

<210> SEQ ID NO 6
<211> LENGTH: 289
<212> TYPE: PRT
<213> ORGANISM: Homo sapiens

<400> SEQUENCE: 6

Met Met Ser Tyr Leu Lys Gln Pro Pro Tyr Ala Val Asn Gly Leu Ser
  1               5                  10                  15

Leu Thr Thr Ser Gly Met Asp Leu Leu His Pro Ser Val Gly Tyr Pro
```

-continued

```
                    20                  25                  30
Ala Thr Pro Arg Lys Gln Arg Arg Glu Arg Thr Thr Phe Thr Arg Ala
            35                  40                  45
Gln Leu Asp Val Leu Glu Ala Leu Phe Ala Lys Thr Arg Tyr Pro Asp
        50                  55                  60
Ile Phe Met Arg Glu Glu Val Ala Leu Lys Ile Asn Leu Pro Glu Ser
65                  70                  75                  80
Arg Val Gln Val Trp Phe Lys Asn Arg Arg Ala Lys Cys Arg Gln Gln
                85                  90                  95
Gln Gln Gln Gln Gln Asn Gly Gly Gln Asn Lys Val Arg Pro Ala Lys
            100                 105                 110
Lys Lys Thr Ser Pro Ala Arg Glu Val Ser Ser Glu Ser Gly Thr Ser
        115                 120                 125
Gly Gln Phe Thr Pro Pro Ser Ser Thr Ser Val Pro Thr Ile Ala Ser
    130                 135                 140
Ser Ser Ala Pro Val Ser Ile Trp Ser Pro Ala Ser Ile Ser Pro Leu
145                 150                 155                 160
Ser Asp Pro Leu Ser Thr Ser Ser Ser Cys Met Gln Arg Ser Tyr Pro
                165                 170                 175
Met Thr Tyr Thr Gln Ala Ser Gly Tyr Ser Gln Gly Tyr Ala Gly Ser
            180                 185                 190
Thr Ser Tyr Phe Gly Gly Met Asp Cys Gly Ser Tyr Leu Thr Pro Met
        195                 200                 205
His His Gln Leu Pro Gly Pro Gly Ala Thr Leu Ser Pro Met Gly Thr
    210                 215                 220
Asn Ala Val Thr Ser His Leu Asn Gln Ser Pro Ala Ser Leu Ser Thr
225                 230                 235                 240
Gln Gly Tyr Gly Ala Ser Ser Leu Gly Phe Asn Ser Thr Thr Asp Cys
                245                 250                 255
Leu Asp Tyr Lys Asp Gln Thr Ala Ser Trp Lys Leu Asn Phe Asn Ala
            260                 265                 270
Asp Cys Leu Asp Tyr Lys Asp Gln Thr Ser Ser Trp Lys Phe Gln Val
        275                 280                 285
Leu
```